United States Patent
Schutz

(10) Patent No.: US 10,310,212 B2
(45) Date of Patent: Jun. 4, 2019

(54) SURGICAL MICROSCOPE STAND

(71) Applicant: Leica Microsystems (Schweiz) AG, Heerbrugg (CH)

(72) Inventor: Marco Schutz, Rorschach (CH)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 0 days.

(21) Appl. No.: 15/126,842

(22) PCT Filed: Mar. 19, 2015

(86) PCT No.: PCT/EP2015/055753
§ 371 (c)(1),
(2) Date: Sep. 16, 2016

(87) PCT Pub. No.: WO2015/140241
PCT Pub. Date: Sep. 24, 2015

(65) Prior Publication Data
US 2017/0097488 A1    Apr. 6, 2017

(30) Foreign Application Priority Data
Mar. 19, 2014   (DE) .................. 10 2014 103 758

(51) Int. Cl.
*G02B 7/00* (2006.01)
*G02B 21/00* (2006.01)
*A61B 90/25* (2016.01)

(52) U.S. Cl.
CPC .............. *G02B 7/001* (2013.01); *A61B 90/25* (2016.02); *G02B 21/0012* (2013.01)

(58) Field of Classification Search
CPC . G02B 7/00; G02B 7/001; G02B 7/02; G02B 21/241; G02B 21/24; G02B 21/22;
(Continued)

(56) References Cited

U.S. PATENT DOCUMENTS

| 7,480,093 B2 | 1/2009 | Sander |
| 2005/0041282 A1 | 2/2005 | Rudolph et al. |

(Continued)

FOREIGN PATENT DOCUMENTS

| CN | 102662229 A | 9/2012 |
| CN | 103315818 A | 9/2013 |

(Continued)

OTHER PUBLICATIONS

International Searching Authority, International Search Report for PCT/EP2015/055753 dated May 20, 2015.

(Continued)

*Primary Examiner* — Jie Lei
(74) *Attorney, Agent, or Firm* — Hodgson Russ LLP

(57) ABSTRACT

The invention relates to a surgical microscope stand (100) encompassing: a first carriage (16) that is arranged on a first carrier arm (14) and is drivable by a first drive unit; and a second carriage (18) that is arranged on a second carrier arm (22) and is drivable by a second drive unit. The surgical microscope stand (100) further encompasses an operating region (34) within which at least one operating unit for manual application of control to the first and second drive units is provided.

9 Claims, 3 Drawing Sheets

(58) Field of Classification Search
CPC .. G02B 21/00; G02B 21/0012; G02B 25/002; G02B 23/125; A61B 90/25; A61B 19/5223; A61B 3/024; A61B 3/02; A61B 3/18; A61B 3/1015
USPC ....... 359/384, 272, 368, 369, 382, 809, 810, 359/815, 819; 351/225, 244, 245, 246
See application file for complete search history.

(56) References Cited

U.S. PATENT DOCUMENTS

| | | | |
|---|---|---|---|
| 2006/0238857 A1* | 10/2006 | Sander | G02B 7/001 359/368 |
| 2006/0250684 A1 | 11/2006 | Sander | |
| 2008/0204864 A1 | 8/2008 | Sander | |
| 2009/0219613 A1* | 9/2009 | Enge | G02B 7/001 359/384 |

FOREIGN PATENT DOCUMENTS

| | | |
|---|---|---|
| DE | 9204118 | 5/1992 |
| DE | 10133018 | 1/2003 |
| DE | 102005018431 | 10/2006 |
| DE | 102008011638 | 9/2009 |
| DE | 102012202303 | 8/2013 |
| EP | 2082700 | 7/2009 |
| JP | 2001-46399 A | 2/2001 |
| JP | 2003111776 A | 4/2003 |
| JP | 2006297098 A | 11/2006 |
| JP | 2006301646 A | 11/2006 |
| JP | 2009201996 A | 9/2009 |

OTHER PUBLICATIONS

International Searching Authority, Written Opinion for PCT/EP2015/055753 dated Sep. 20, 2015.

* cited by examiner

SURGICAL MICROSCOPE STAND

CROSS-REFERENCE TO RELATED APPLICATIONS

The present application is the U.S. national phase of International Application No. PCT/EP2015/055753 filed Mar. 19, 2015, which claims priority of German Application No. 10 2014 103 758.8 filed Mar. 19, 2014, the entirety of which is incorporated herein by reference.

FIELD OF THE INVENTION

The invention relates to a surgical microscope stand having a first carriage that is arranged on a first carrier arm and is drivable by a first drive unit, and a second carriage that is arranged on a second carrier arm and is drivable by a second drive unit.

BACKGROUND OF THE INVENTION

Known stands for surgical microscopes comprise a suspension apparatus that encompasses a total of three movable carriages. In particular, a so-called A carriage, a B carriage, and a C carriage are provided, so that a motion in all three spatial directions is possible. The carriages are moved in this context via motors, a separate motor being provided to move each carriage.

In addition to automatic counterbalancing, the individual carriages can also be displaced manually; a toggle switch with which the pertinent carriage can be displaced in both of its directions in order to effect a new counterbalancing operation, or for balance adjustment, is provided for each carriage on the arm pertinent thereto.

A possible counterbalancing mechanism for a surgical microscope stand is commonly known to one skilled in the art and will not be described in further detail here.

These known stands have the disadvantage that a pressure is exerted by each actuation of the toggle switch in the context of manual counterbalancing, thereby making accurate counterbalancing difficult. An elevated pressure upon actuation of the toggle switch is necessary in particular when the surgical microscope stand is enclosed by a so-called "drape," with the result that manual counterbalancing can be accomplished only very inaccurately. The toggle switches moreover have the disadvantage that dirt can quickly become lodged in them, and they are difficult to clean in thoroughly hygienic fashion. A further disadvantage of these known stands is that depending on the position of the carrier arms of the suspension apparatus, the toggle switches are difficult to access, and in particular the toggle switches for different carriages are located at sites far apart from one another. This results in a space-intensive and motion-limiting configuration. A further disadvantage of these stands is that the motors usually can be actuated as desired with the carrier arms in any position, which can lead to overheating of the motors due to overload of the motors. The service life of the motors is thereby limited, and considerable noise emission can occur.

SUMMARY OF THE INVENTION

An object of the invention is to describe a surgical microscope stand that, inter alia, enables simple operation and reliable manual counterbalancing.

This object is achieved by a surgical microscope stand having an operating region within which at least one operating unit for manual application of control to the first and second drive units is provided. Advantageous refinements of the invention are described in the specification.

According to the present invention the surgical microscope stand encompasses an operating region within which at least one operating unit for manual application of control to the first and second drive units is provided. Thanks to the arrangement of the at least one operating unit for controlling the first and second drive unit within one and the same operating region, a compact operating region for manual application of control to the drive units is achieved. This enables quick and efficient balancing (adjustment) during a surgical procedure. This also provides the advantage that by viewing the one operating region, the user of the stand has in his or her field of view all the operating elements necessary for balancing or adjustment.

Usually the surgical microscope stand is automatically counterbalanced before a surgical procedure begins. This is done, for example, by operating an operating element that can be arranged in the above-described operating region. It is also possible, however, to embody this operating element for automatic counterbalancing of the stand outside the operating region. Particularly preferably, the operating element for automatic counterbalancing is embodied not only at one region but at multiple regions of the stand. Another counterbalancing operation may be necessary during a surgical procedure because the center of gravity of the stand changes, for example due to displacement of a microscope tube. In order to achieve this new counterbalance the user (as a rule, the surgeon) applies control manually to the respective carriage via an operating element that is provided. The aforesaid operating region is provided on the stand for this direct and manual application of control. Mounting the operating elements for all the carriages within one and the same operating region results in an efficient and compact configuration of the operating elements for manual application of control, and at the same time implements user-friendly operation of the respective carriages. The size of the operating region can correspond, for example, to the area that is needed in order to mount all the necessary operating elements next to one another.

According to a preferred embodiment of the invention, the stand encompasses only a single operating unit with which control can be applied both to the first and to the second drive unit, i.e. with which both the first and the second carriage can be moved. This has the advantage that multiple separate operating units for each carriage are not necessary, but instead central operation of all drive units is made possible. Operating convenience is thereby enhanced.

According to a further embodiment the operating unit for manual application of control to the carriages is embodied by a touchscreen arranged in the operating region. The use of a touchscreen has the advantage that, compared with toggle switches and the like, only a very small pressure needs to be applied, and the process of manually counterbalancing the surgical microscope stand is thus not negatively affected. Preferably the touchscreen is a resistive touchscreen. Such touchscreens can also be operated with minimal pressure through a drape. In addition, such touchscreens enable particularly good cleaning, so that hygiene is enhanced. The touchscreen furthermore provides the advantage that only relevant information can be displayed. For example, operating fields are displayed only for those carriages which, according to a calculation of a control unit, are in fact movable based on their current position. This prevents transmission of excessive information to the user. This has the advantage that the user can maintain a high level of concentration during the surgical procedure. In the context of implementation of the operating elements via a touchscreen, the size of the operating region preferably corresponds to the size (area) of the touchscreen.

According to a particularly preferred embodiment of the invention the surgical microscope stand encompasses a third carriage and a third drive unit for driving the third carriage, the operating unit for manual application of control to the third carriage being arranged within the operating region. The operating unit of the third drive unit is thus also preferably arranged within the operating region, thereby making it possible to displace the surgical microscope in all three directions by operating only a single operating region and preferably a single operating element.

In a particularly preferred embodiment a location sensor is provided on at least one of the carriages for ascertaining the location of that carriage in space. By way of the location sensor the position of that carriage, and thereby also the position of the other carriages, can be accurately determined at any time.

The location sensor is arranged in particular on the carriage on which the microscope is mounted. This has the advantage that the position of all carriages relative to a zero level can be determined with the aid of only a single location sensor, since a location can respectively be associated uniquely with a position of all three carriages.

In an alternative embodiment of the invention multiple location sensors can also be provided. In particular, a separate location sensor, with which only the location of the respective carriage is ascertained, can also be provided on each carriage.

It is particularly advantageous if the location ascertained with the aid of the location sensor is displayed via the operating unit to an operator, so that the latter can recognize at any time the exact position of the individual carriages.

In a particularly preferred embodiment a predetermined permissible displacement range relative to a zero position is stored for at least one carriage in a control unit of the stand. The control unit is designed in such a way that it permits, upon operation of the operating unit, a movement of the carriage only within that displacement range. It is particularly advantageous if a respective permissible displacement range is predetermined for each carriage, and if displacement is possible only within that respective displacement range. The result thereof is that overheating is avoided and actuation of the drive unit is possible only in the respective displacement range, so that in particular there is no need to limit the motion of the individual carriages by way of stops.

It is particularly advantageous if the control unit compares the location ascertained with the aid of the location sensor with the predetermined permissible displacement range and, depending on the result of that comparison, authorizes a displacement of the respective carriage only when the latter is located within the permissible displacement range. In particular, only one displacement direction for the respective carriages can also be authorized depending on the result of the comparison.

Authorization can be accomplished in particular by the fact that a corresponding operating symbol is displayed in the operating region, preferably on the touchscreen, only when a displacement is in fact permissible; and that no operating symbols at all are displayed in the case in which no displacement is permissible. Alternatively, the symbols can also always be displayed, and can be characterized differently for the case in which displacement is not permissible. For example, the symbols can have a gray background or can be faded, so that the user knows intuitively that that displacement is not permissible at the moment.

The operating unit can furthermore also display information as to whether a displacement of the carriage in the respective direction is permissible. This can be done, for example, via a text or via symbols.

In a particularly preferred embodiment a control unit of the surgical microscope stand ascertains, depending on preset criteria and on the location respectively ascertained in real time, which carriages are allowed to be moved and which not. In particular, the control unit is programmed so that carriages are not allowed to be displaced if they are oriented so that there is an excessive weight load on the respective drive unit or the drive unit must generate an excessive driving force. Overloading of the respective drive unit is thereby avoided. In particular, only a respective carriage that currently can be displaced is ever displayed. Only when the latter is correspondingly displaced, or when the arm is correspondingly rotated so that the weight load on the drive unit of the other carriage is no longer so great, can the other carriages, or one of the other carriages, also be authorized for operation.

It is particularly advantageous if the operating unit respectively displays information as to which carriages are currently allowed to be displaced.

The location sensor is, in particular, a gravitation sensor with which an accurate determination of the respective location is possible in simple fashion.

The displacement ranges within which the carriages can be displaced are safeguarded in particular via light barriers, i.e. a determination is made with the aid of light barriers as to whether a carriage has arrived at the end of a displacement range, and the corresponding drive unit is then automatically deactivated.

It is furthermore advantageous if further information is displayed via the operating unit, in particular via the touchscreen. In particular, information regarding counterbalancing of the stand, illumination, video images, working distance, magnification, and/or warning messages, are displayed. All motions of the stand, and at the same time all information outputs, can thus be effected with the aid of one operating unit at a central location, thereby substantially simplifying operation.

It is furthermore advantageous if a mounting unit for mounting a microscope is provided on one of the carriages, and if the operating region is arranged above that mounting unit. What is achieved thereby is that the operating unit can be easily operated and viewed at any time, since an operator simply needs to look up from the actual microscope and obtains information and can carry out all operations.

Preferably the operating region is embodied on the first carrier arm. This has the advantage, among others, that a motion of the carriage has no influence on the position of the operating region. Upon actuation of the operating element, preferably of the touchscreen, within the operating region, the operating region therefore nevertheless remains in its current location. Operation of the operating region furthermore does not influence the counterbalancing operation itself, since the first carrier arm constitutes a neutral site. The pressure that is applied to the stand or to the carrier by the user as a result of operation of the operating region does not exert any torque that needs to be considered in the context of balance adjustment.

BRIEF DESCRIPTION OF THE DRAWING VIEWS

Further features and advantages of the invention are evident from the description that follows, which explains the invention in more detail with reference to exemplifying embodiments in conjunction with the attached Figures, in which.

DETAILED DESCRIPTION OF THE INVENTION

Figure 1:
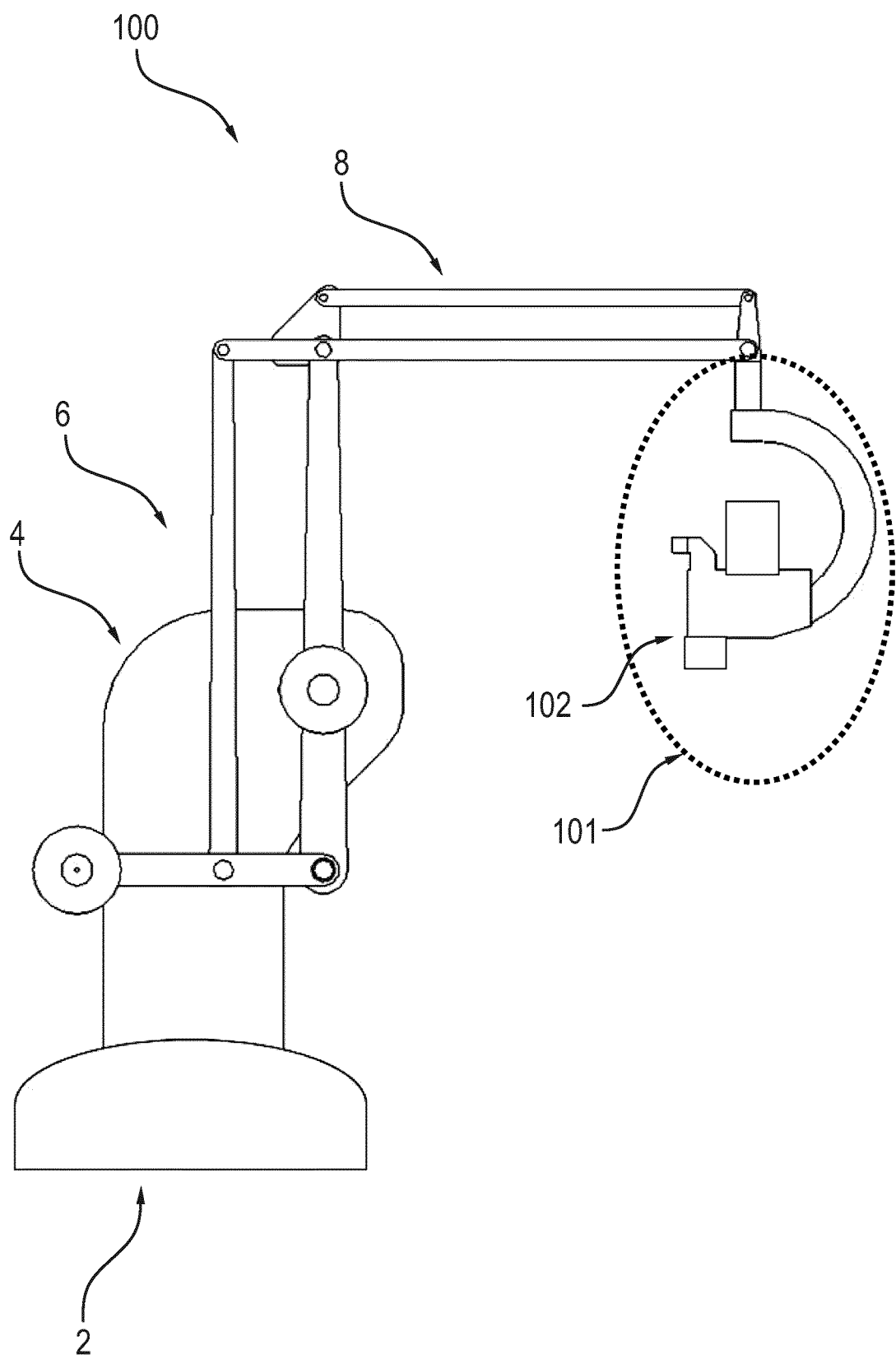
FIG. 1 is a simplified depiction of a known surgical microscope stand.

FIG. 1 shows, merely in simplified fashion, a portion of the structure of a known surgical microscope stand 100 having a stand base 2, a support column 4, a first articulated arm 6, and a second articulated arm 8, articulated arms 6, 8 each being constituted by so-called parallel members. Suspended at the free or distal end of second articulated arm 8 is a suspension apparatus 101 that encompasses, inter alia, a surgical microscope 102. A control unit (not depicted) is accommodated, for example, in support column 4.

A configuration of this kind is known, for example, from DE 10 2012 202 303 A1, which only describes a possibility for a counterbalancing mechanism.

Figure 2:
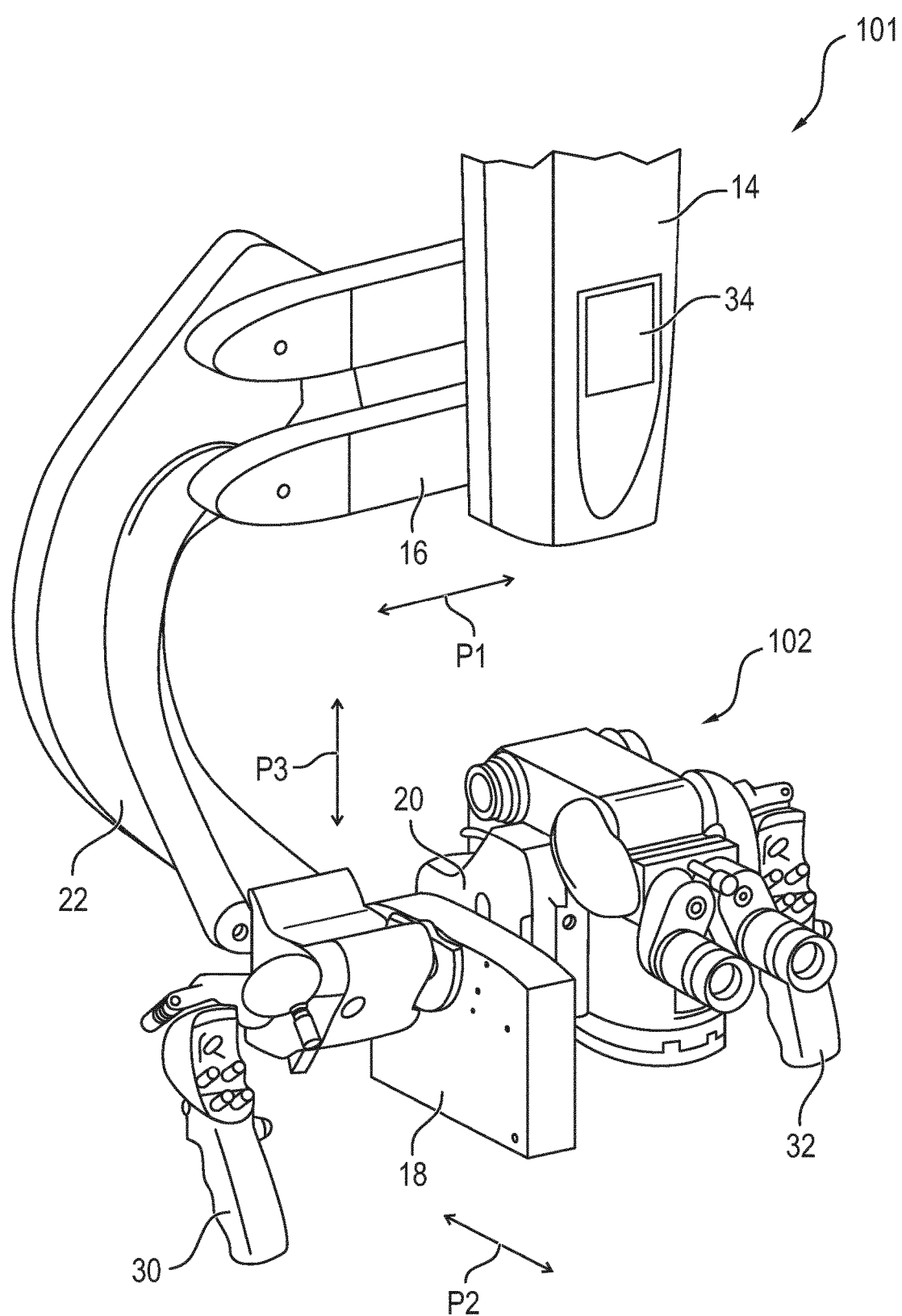
FIG. 2 is a schematic perspective depiction of a suspension apparatus of a surgical microscope stand according to a first embodiment of the invention.

FIG. 2 is a schematic perspective depiction of a suspension apparatus 101 of a surgical microscope stand according to a first embodiment of the invention, which stand encompasses a surgical microscope 102.

Figure 3:
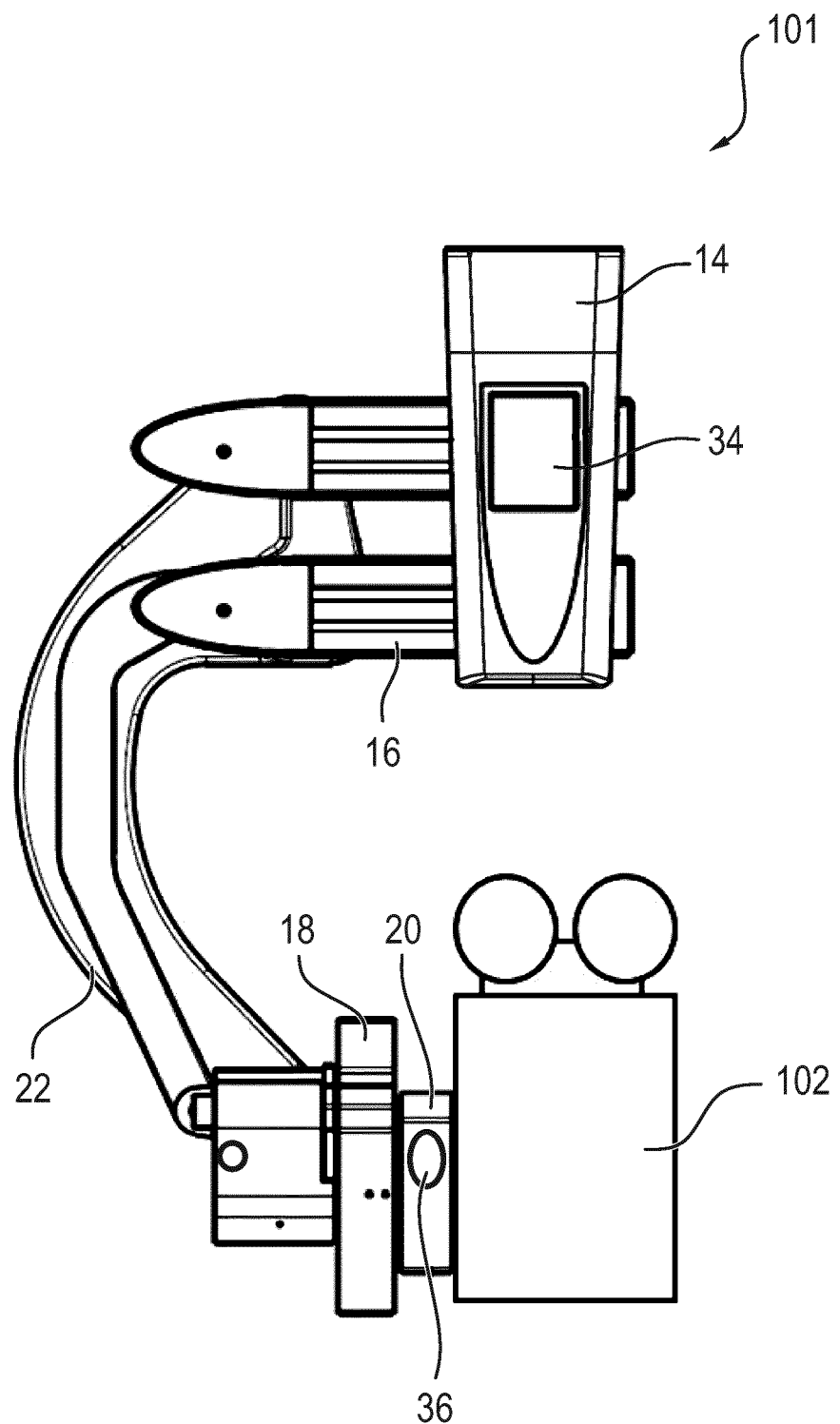
FIG. 3 schematically depicts a suspension apparatus of a surgical microscope stand according to a second embodiment of the invention.

FIG. 3 schematically depicts a suspension apparatus 101 according to a second embodiment that is very similar to the first embodiment. This suspension apparatus 101 also encompasses a surgical microscope 102. Elements having an identical configuration or identical function have the same reference characters.

Suspension apparatus 101 encompasses a first carrier arm 14 and a second carrier arm 22. First carrier arm 14 is connected at its first end to second articulated arm 8 and at its other, second end to a first carriage 16.

First carriage 16 is displaceable or movable relative to first support arm 14 in the direction of double arrow P1. Mounted in turn on first carriage 16 is second carrier arm 22, which is correspondingly moved together with first carriage 16 in the direction of double arrow P1. Second carrier arm 22 is in particular arranged rotatably on first carriage 16.

Arranged in turn on second carrier arm 22 is a second carriage 18, which is supported movably in the direction of a double arrow P2 relative to second carrier arm 22. A further, third carriage 20 is mounted directly on second carriage 18 and is displaceable relative thereto in the direction of double arrow P3. The directions P1, P2, and P3 are in particular all oriented mutually orthogonally, so that a displacement in all spatial directions is possible.

A displaceability of surgical microscope 102 is achieved by way of suspension apparatus 101 having carriages 16, 18, and 20, so that said microscope can be adapted to particular circumstances in terms of the surgical procedure and the height of the surgeon.

Carriages 16, 18, and 20 are displaced in particular via drive units, for example electric motors, each carriage 16, 18, and 20 having associated with it a separate motor with which only it is displaced. The motors are not visible in FIGS. 1 to 3, since they are arranged in concealed fashion inside the housing in order to prevent damage. Stand 100 according to the first embodiment shown in FIG. 2 furthermore encompasses grips 30, 32 with which surgical microscope 102 can be moved.

An operating region, within which an operating unit embodied as touchscreen 34 is arranged, is embodied on first carrier arm 14. Control can be applied manually to all three motors via this touchscreen 34, so that it is possible to move all the carriages 16, 18, and 20 via only the one operating unit 34. In this exemplifying embodiment the size of the operating region corresponds to the size (or area) of touchscreen 34.

This has the advantage that the number of operating units is reduced, and the wiring and overall configuration are therefore also simplified. Operating convenience is furthermore appreciably enhanced, since displacement of each carriage no longer requires, as it did previously, actuation of a separate operating element arranged on it or in its vicinity.

The arrangement of touchscreen 34 on first carrier arm 14 furthermore has the advantage that pressure on touchscreen 34 does not negatively affect the counterbalancing of the surgical microscope. The position of touchscreen 34 moreover remains fixed, so that the operator does not need to adjust to a modified location upon displacement of surgical microscope 102.

In addition, appreciably enhanced hygiene is achieved by the use of a touchscreen 34 as compared with usual toggle switches or similar knobs, since such a touchscreen 34 can be cleaned easily and with no residue and exhibits no crannies in which dirt can become lodged. A touchscreen 34 of this kind can furthermore be operated easily and reliably even when the surgical microscope stand is enclosed in a "drape."

Provided on third carriage 20 is a location sensor 36 with which the location of that third carriage 20 in space can be ascertained, in particular relative to a predetermined zero orientation. The locations and positions of the other carriages 16, 18, and of the other carrier arms of the suspension apparatus, can also be determined by way of the ascertained location of third carriage 20.

The location ascertained via location sensor 36 is transmitted in particular to the control unit, which determines the corresponding orientations of the other carriages 16, 18 depending on the ascertained location of third carriage 20 and compares the respective orientation of the individual carriages 16 to 20 with preset displacement ranges. These displacement ranges are predetermined in such a way that they indicate which location the individual carriages 16 to 20 are allowed to be manually displaced into, and which location they correspondingly are not to be moved into. The displacement ranges are selected in particular in such a way that the individual carriages 16 to 20 can be displaced only if they are loaded with the least possible weight, or conversely that it is not permitted to move those carriages 16 to 20 for which, because of their current orientation, there is an excessive weight load on the drive unit associated with the respective carriage 16 to 20, or for which the drive unit must generate an elevated driving force in order to drive carriages 16 to 20.

Carriages 16 to 20 furthermore have, as a result of their mounting on carrier arms 14, 22, a mechanically predefined positioning range within which they can be displaced. This mechanically limited displacement capability is also taken into account within the displacement ranges stored in the control unit, so that the control unit permits an actuation of one of carriages 16 to 20 in one of the respective directions P1 to P3 only if they are not already at a stop. This can also be monitored and controlled in particular with the aid of light barriers.

The control unit is in particular programmed in such a way that a respective indication is given as to which carriage or carriages 16 to 20 is or are currently allowed to be displaced. The other carriages 16 to 20 that are not allowed to be displaced are, in particular, not displayed at all. In addition, for those carriages which are allowed to be displaced, corresponding operating elements whose actuation makes it possible to move that carriage 16 to 20 in its corresponding direction P1 to P3 are shown via touchscreen 34. If carriage 16 to 20 can be moved in only one direction because of its position, however, the other symbol is shown in faded fashion or with a gray background, so that the operator knows that movement is possible in only the one direction. If none of the carriages is allowed to be displayed given the respective positions of the carriages, this is likewise indicated to the user.

Thanks to this limitation of the displacement possibilities for the individual carriages 16 to 20 to the respective directions that are currently useful, overheating of the motors is avoided and their service life is thus increased. Unnecessary noise emission is furthermore suppressed from the outset.

In addition to the individual displacement possibilities, a plurality of additional information items can also be displayed to the operator via touchscreen 34. For example, it is possible to display whether surgical microscope stand 100 is in a counterbalanced state, what the current individual positions of carriages 16 to 20 are, whether illumination systems and/or video captures are activated, and/or what the current working distance of surgical microscope 102 is. Warning notifications, for example, can also be displayed via touchscreen 34.

The operator is thus provided, via only one touchscreen 34, on the one hand with the ability to operate all the drive units of stand 100, and on the other hand with a central site through which as much as possible of the information relevant to him or her is displayed.

A usual use of surgical microscope stand 100 is outlined briefly below. Before the surgical procedure begins and after the desired surgical microscope 102 is attached, stand 100 is automatically counterbalanced. This is accomplished by means of a button that can be arranged, for example, on the support column. An operating element of this kind can also, however, be implemented via touchscreen 34.

Once automatic counterbalancing has been carried out, the surgical microscope stand is ready for use. It may be desirable during the surgical procedure to carry out a balance adjustment, for example because the microscope tube has been shifted during the procedure. In order to achieve counterbalancing again, control can then be applied to carriages 16 to 20 directly via touchscreen 34. Symbols for application of control to the respective carriages 16 to 20 are displayed in touchscreen 34, and the user can move the desired carriages 16 to 20 by manual input in order to achieve counterbalancing again.

The user needs to observe only one operating region, and obtains from it all the information needed in order to quickly counterbalance the surgical microscope stand again by manual application of control to the respective carriages.

LIST OF REFERENCE CHARACTERS

2 Stand base
4 Support column
6, 8 Articulated arms
14, 22 Carrier arms
16, 18, 20 Carriage
30, 32 Grip
34 Touchscreen
36 Location sensor
100 Surgical microscope stand
101 Suspension apparatus
102 Surgical microscope
P1, P2, P3 Direction

The invention claimed is:

1. A surgical microscope stand (100) comprising:
a first carriage (16) that is arranged on a first carrier arm (14) and is drivable by a first drive unit; and
a second carriage (18) that is arranged on a second carrier arm (22) and is drivable by a second drive unit;
wherein the surgical microscope stand (100) further comprises an operating region within which an operating unit for manual application of control to the first and second drive units is provided, wherein the operating region is located on the first carrier arm; and
wherein the operating unit is configured to enable an operator to individually select a respective displacement direction (P1, P2) for each of the first and second drive units and to individually apply control to each of the first and second drive units to independently displace the first carriage (16) and the second carriage (18) in the respective displacement direction; and
wherein a location sensor (36) is provided on at least one of the carriages (16, 18) for ascertaining a location in space of the at least one carriage; and
wherein a predetermined permissible displacement range relative to a zero position is stored for the at least one carriage (16, 18) in a control unit of the stand (100), and a movement of the at least one carriage (16, 18) by actuation of the operating unit is possible only within the predetermined permissible displacement range; and
wherein the control unit compares the location in space ascertained by the location sensor (36) with the predetermined permissible displacement range and, depending on a result of that comparison, authorizes a displacement of the at least one carriage (16, 18).

2. The surgical microscope stand (100) according to claim 1, further comprising a third carriage (20) and a third drive unit for driving the third carriage (20), wherein the operating unit is operable for manual application of control to the third carriage (20).

3. The surgical microscope stand (100) according to claim 2, the location sensor (36) being arranged on one of the carriages (16, 18, 20) on which a surgical microscope (102) is mountable.

4. The surgical microscope stand (100) according to claim 2, the ascertained location being displayable with the aid of the operating unit.

5. The surgical microscope stand (100) according to claim 2, a respective predetermined permissible displacement range relative to a zero position being stored for each carriage (16, 18, 20) in the control unit; and a movement of the respective carriage (16, 18, 20) by actuation of the operating unit being authorized only within the respective displacement range.

6. The surgical microscope stand (100) according to claim 5, the operating unit displaying information as to whether a displacement of the carriages (16, 18, 20) in the respective directions (P1, P2, P3) is permissible.

7. The surgical microscope stand (100) according to claim 6, the control unit defining, depending on positions of the carriages ascertained in real time, which carriages (16, 18, 20) are movable, and correspondingly controlling an information display on the operating unit.

8. The surgical microscope stand (100) according to claim 1, a display unit (34) being provided within the operating region, which unit displays information regarding counterbalancing of the stand, illumination, video images, working distance, magnification, and/or warning messages.

9. The surgical microscope stand according to claim 1, wherein a mounting unit for mounting a surgical microscope (102) is arranged on one of the carriages (16, 18); and the operating region (34) is provided above that mounting unit.

* * * * *